(12) United States Patent
Cheng et al.

(10) Patent No.: US 9,085,768 B2
(45) Date of Patent: Jul. 21, 2015

(54) **APPLICATION OF THE BROCCOLI WOUND-INDUCIBLE PROMOTER OF *GLUCOSE INHIBITION OF ROOT ELONGATION 1* GENE IN TRANSGENIC PLANTS**

(75) Inventors: Wan-Hsing Cheng, New Taipei (TW); Ming-Hau Chiang, Taipei (TW); Ya-Huei Chen, New Taipei (TW); Hwei-Ling Shen, New Taipei (TW)

(73) Assignee: Academia Sinica, Taipei (TW)

( * ) Notice: Subject to any disclaimer, the term of this patent is extended or adjusted under 35 U.S.C. 154(b) by 340 days.

(21) Appl. No.: 13/572,541

(22) Filed: Aug. 10, 2012

(65) Prior Publication Data

US 2014/0013472 A1    Jan. 9, 2014

Related U.S. Application Data

(60) Provisional application No. 61/522,484, filed on Aug. 11, 2011.

(51) Int. Cl.
*C12N 15/82* (2006.01)
*C12N 15/113* (2010.01)
*C07H 21/04* (2006.01)

(52) U.S. Cl.
CPC .......... *C12N 15/113* (2013.01); *C12N 15/8209* (2013.01); *C12N 15/8237* (2013.01)

(58) Field of Classification Search
None
See application file for complete search history.

(56) References Cited

U.S. PATENT DOCUMENTS

2005/0244968 A1\* 11/2005 Perera et al. .................. 435/419
2008/0263721 A9\* 10/2008 Boukharov et al. ........... 800/278

OTHER PUBLICATIONS

Wu_Planta_v229_p1231_2009.*
Donald_EMBO J_9_1717_1990.*
Dolferus_Plant Phys_105_1075_1994.*
Kim_Plant Mol Biol_24_105_1994.*
Potenza_In Vitro Cell Dev Biol Plant_40_1_2004.*

\* cited by examiner

*Primary Examiner* — Medina A Ibrahim
*Assistant Examiner* — Russell Boggs
(74) *Attorney, Agent, or Firm* — Drinker Biddle & Reath LLP

(57) ABSTRACT

In this study, we used a wound-inducible promoter of the broccoli (*Brassica oleracea* var. *italica*) GLUCOSE INHIBITION of ROOT ELONGATION1 (GIR1) gene fused to β-glucuronidase (GUS, pBoGIR1::GUS) as a selectable marker. Transgenic broccoli plants expressing pBoGIR1::GUS appear blue in planta at wounded regions after GUS staining for 30 min. Similarly, the blue color is visible in transgenic *Arabidopsis* and rice plants expressing pBoGIR1::GUS at wounded areas after GUS staining for 2 h, indicating that this promoter is wound-inducible in both dicots and monocots. GUS staining is very rapid and the partial wounding in this study is a nondestructive method that does not affect further plant growth and development. Thus, pBoGIR1::GUS could serve as an effective substitute for antibiotic- and herbicide-resistance genes in the generation of genetically modified crops.

16 Claims, 8 Drawing Sheets

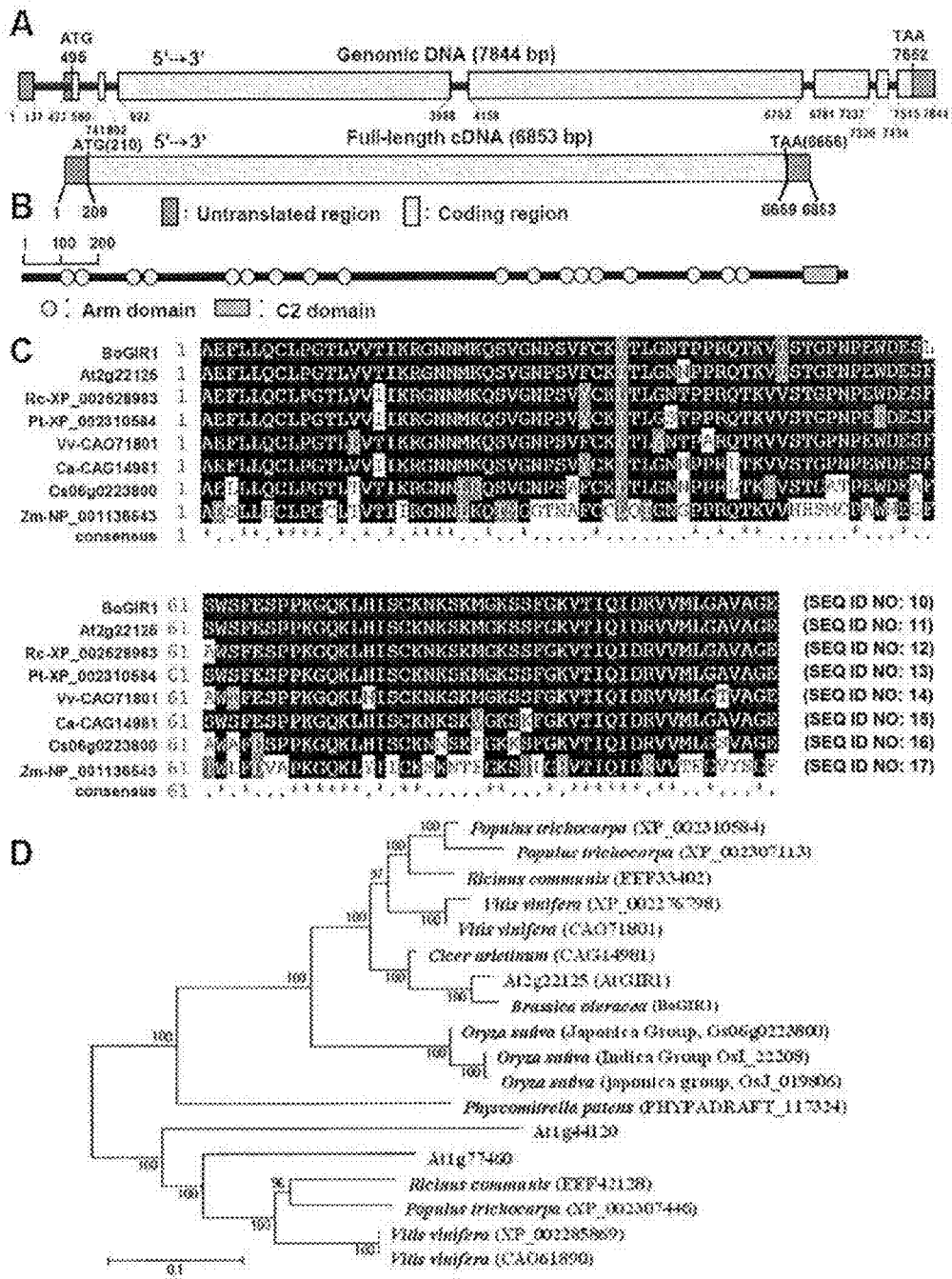
Figure 1. Gene structure, amino acid alignment, and phylogenetic analysis of BoGIR1 and its homologs among plant species.

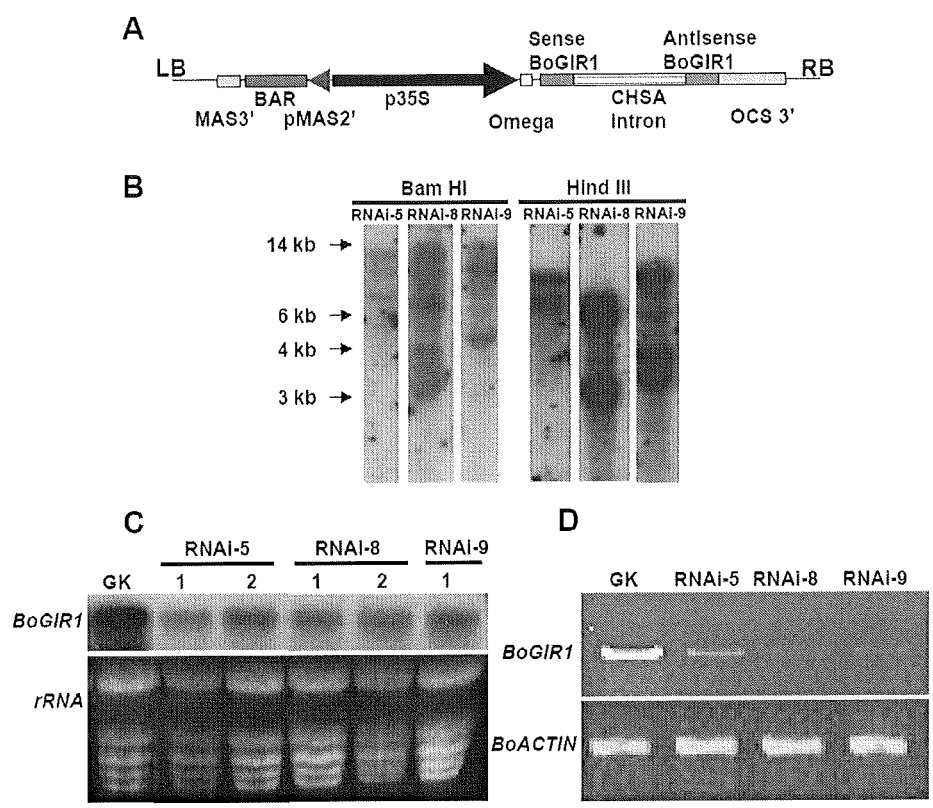
Figure 2. *RNAi* transgene and analysis of *RNAi* transgenic plants

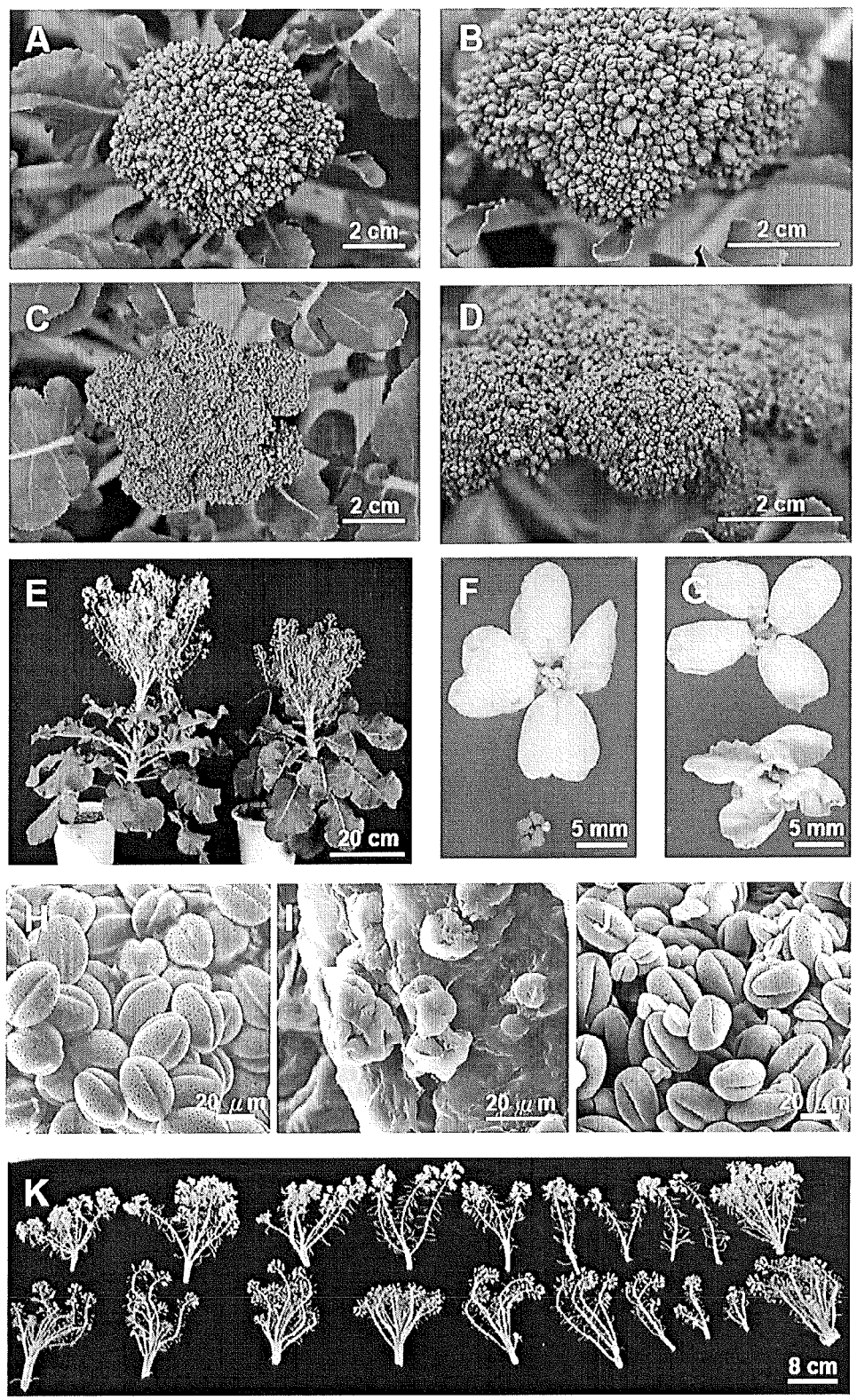
Figure 3. Phenotypic comparison of wild-type and RNAi transgenic plants in broccoli

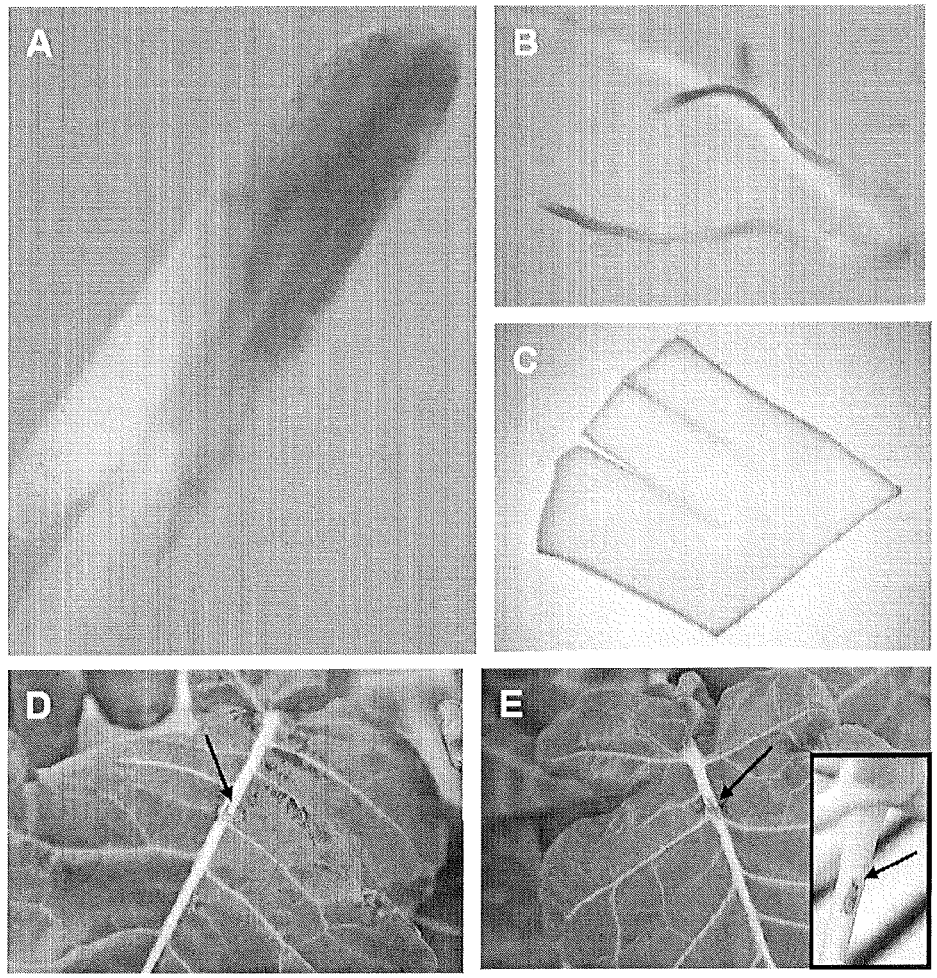
Figure 4. Tissue-specific and wound-inducible expression of *BoGIR1* in broccoli

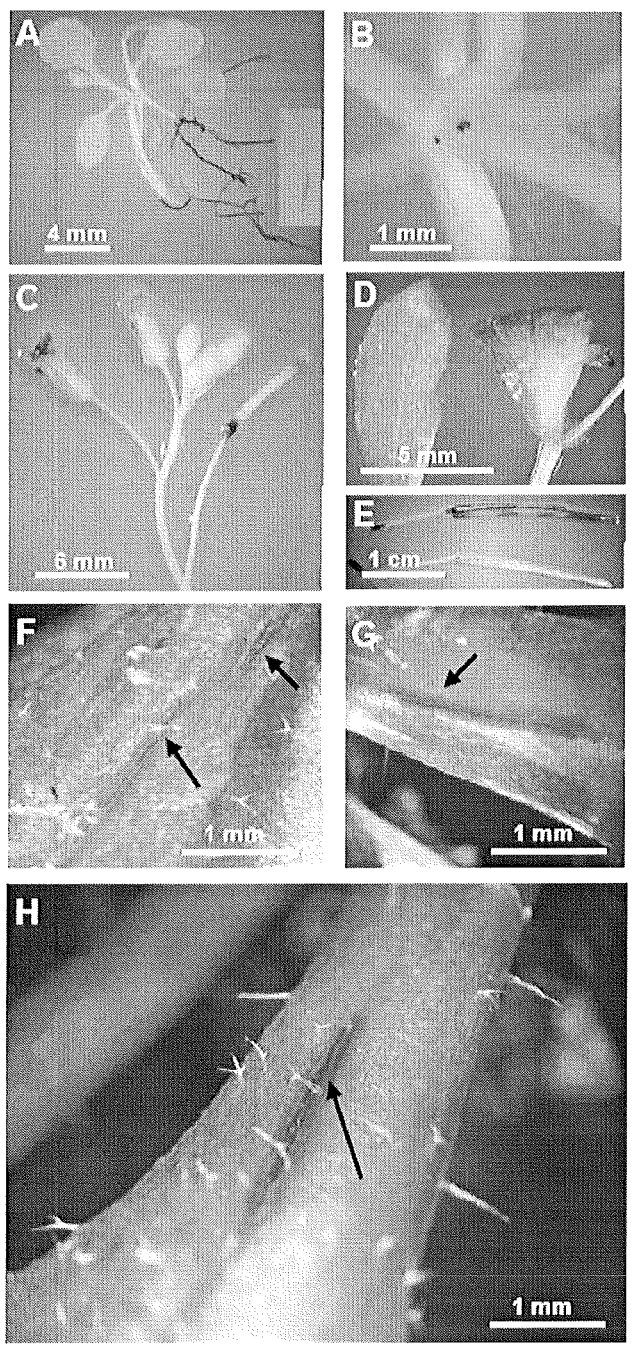
Figure 5. Heterologous expression of *pBoGIR1::GUS* in Arabidopsis transgenic plants

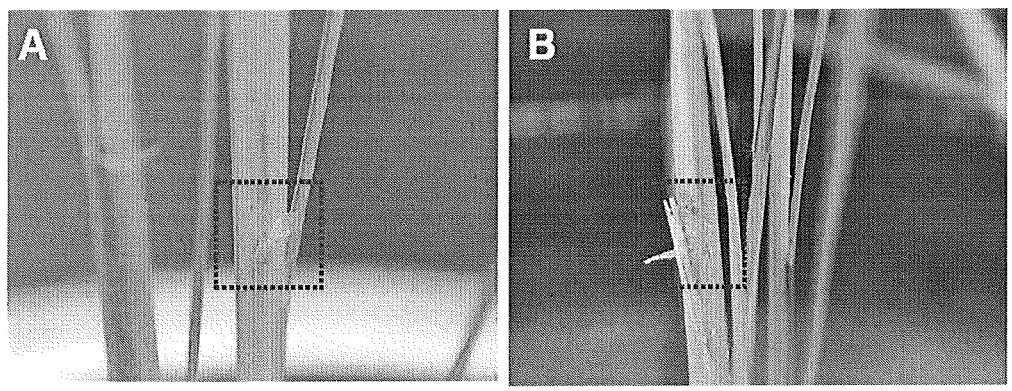
Figure 6. Heterologous expression of pBoGIR1::GUS in rice transgenic plants

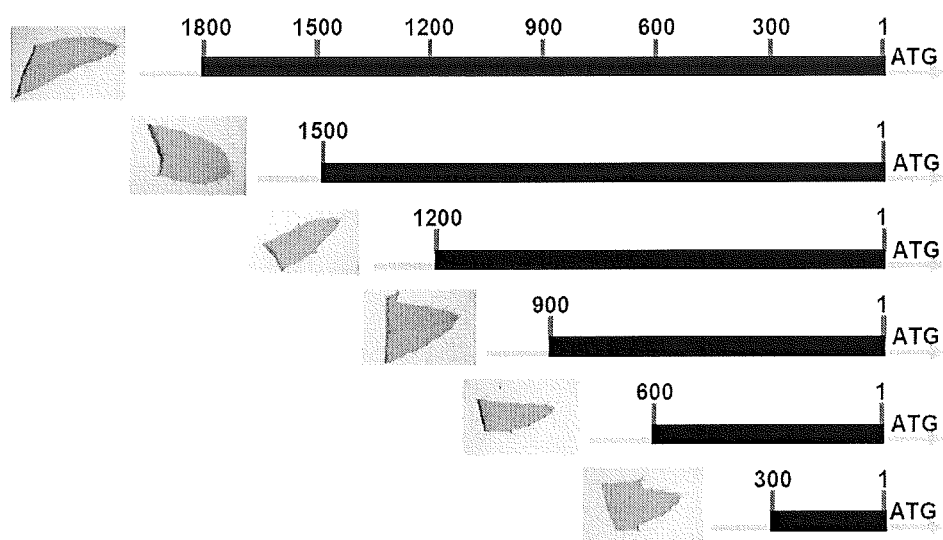
Figure 7. Deletion assay of *BoGIR1* promoter (1880)ATATCGTATGCTTTCATGAGCATAGTTGTCGATAGAAACAAAACATGCGTCGAAGAGAGAAC
TTTGAATCTTTAGTTTATTCCCATTAGCTAGGCATGAGGCCATGTGCTTCTTTGCTCTCCCACGTTATAT
ATTTTACCACTTTGGGACAAAAGAACTGCTGTCAGTTTTCGGACAGCGTAGAAAGATCATGTCAAGG
AAATAATTTACATGTGTAGGAAGCCACATATAAAAAATAATATTACATCCTTATCCACGGGAAGCTA
ATTCGAAATGATTGTGATGTTGACAATTGTTTTTAGTAAATTTTCATAATCGGTTTGGTGGTACATAC
CTTTACTATCGCCATCTTAATGGACTAATCAATCGAGTTTGGTAACTAA (1500)TCAATATATATAGGTCCTATAACAACTACTACAAATCTAATCATTTTTTTTCAACATAGGAAGG
GAAGAAGCCGGATAGTTTGGCATAAAGACAATAAAACTTAGAAAATAAATTGTAAAACAATAAATA
AACAAAAAAGTAAGATGTTTAATTAAGTTTGTATATCTCTATTTGTAACTACATAATTAATTATATTAT
AAGCAAATAAGCAAAAATTAGAAAACTGATTTTTAATAGTATGTTAACAATAATTTGAACAAAAACC
TATACATTATAATTAAGTTTATGATATACTCTCT (1200)TTGTTTCCAAAGATTGATATTTTAGAATTTTTATACATATTAAAAAAATATGAAATTTTGATTA
TCAATATATTATTTTCTGTAACTAACTATTTTCAATAAGTTTTAACCAATAGGCTTTCAATAAACACAA
ATATGTTTTTGAAATTTACAATTTACCAATAATTAATATATTGAAAATGCAAAAAGTATAGTTTTGAA
ACAATATTTTTTAAACATAGATTTTTTCGGAAAGGAGGGAGTAATATTTAAACGTTAGAGTTTAAGG
TTAAAATTTAGAGTAATTTAATTAATATTGTT (900)TAATAATTTTTTTTTTTTTGTGATTTTTTGCCTCTACAATTTTTACGATAATTTTAAATGCTATTAA
TGAAAATTTCTAGGAGTATATATCTAAGTTACAAAAAAAAGGTAGGAGTATAATATTACATTTGTAT
CAGTTACGTGTTTTCACTTGTATAATCAGTGAAATAAATGGCCGATTAGTCGTAATTAGTAGTAAATG
AAGTCAATGTCTCCTCTCATTTGTAATATACAAAATATCGACTCGTTTGGCTAAGCCGATCGGAGCTG
GAGCCGTTTAGTAAATCCAGTCTCTGTCGG (600)TGGATAGGCAAAGCCGGCTCCAATCTGATAACACACTCTCACCAGCCCACACACAGCTCTCTCTC
TCTCCCCTCCGTTTTATACTTATTTTTAAGTCAAATTTTCACAAGAAAGAGAATCCTCTCCCTATCTCTC
TCTCTAAACTGTTCGACTTCTTCGCTTCTCTTCTACGAAACAATCGAATGCACAACTGATTCTGCTCTCT
CCTCCTCCTCCTCCTCCTTCTCGCCATTTTCTCTCTGAGGTTAGTTCAATTCCTCCATCTATGGACCTATC
TTCATGCTTTTAGTACATCGGATC (300)TCTTCTGCGTAGACTGTGTACCAGAATCGTTGATCTCAGTGAGGGATCCGAGTTTTTGAATTAG
ATTCCATCGCGATCTGAGTCCTACATCCGAATCGATAAACTTTCCTGATTTAGATTAGCTCATCAAATC
TGGAAAGTAAAACGATTCGGATCGATAAAAGAGTAATCTATTAGTTAGTATTTATTAATTGCATTTTT
AGCTTCTGATCTGATCTCTTCTTCCAGGGGGAGTTGATACTCTGACGGTATATTCTCGATAGATCTGA
GTAGAGAATCTTTGAAGTGTAACAGAAAAGAATG Figure 8. The Promoter sequences of *BoGIR1* (designated as SEQ ID NO: 1) and its putative wound-inducible *cis*-acting elements. *Cis*-acting elements were searched by PlantCARE(http://bioinformatics.psb.ugent.be/webtools/plantcare/html/) and PLACE (http://www.dna.affrc.go.jp/PLACE/signalscan.html). T/G-boxes are shown in blue with an underline, and the W-box is shown in red with a square. The ATG start codon and a putative TATA box were underlined.

APPLICATION OF THE BROCCOLI WOUND-INDUCIBLE PROMOTER OF *GLUCOSE INHIBITION OF ROOT ELONGATION 1* GENE IN TRANSGENIC PLANTS

PRIORITY

Priority is claimed to U.S. Provisional Application Ser. No. 61/522,484, filed on Aug. 11, 2011. The disclosure of the aforementioned priority application is incorporated herein by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_16024_00020. The size of the text file is 12,396 bytes, and the text file was created on Sep. 18 2013.

BACKGROUND

Field of the Invention

The invention relates to the broccoli wound-inducible promoter of GLUCOSE INHIBITION of ROOT ELONGATION 1 gene and its use in transgenic plants.

BACKGROUND OF THE INVENTION

Introduction

To improve human health and provide sufficient food supplies, scientists worldwide have dedicated themselves to developing plant transgenic techniques for increasing of crop yield, nutrient value, resistance of environmental biotic and abiotic stresses, and other value-added traits. Traditional transgene constructs ordinarily contain antibiotic- or herbicide-resistance genes as selectable markers for isolating transgenic plants from non-transgenic ones. However, the effects of these selectable markers in transgenic plants on human health and environmental contamination have become a major concern to date (Sanjaya et al., 2008a). Thus, the development of a transgene construct that does not use antibiotic- or herbicide-resistance genes in the production of genetically engineering crops is essential for reducing the overuse of antibiotics and herbicides. To this aim, many techniques have been developed, such as co-transformation (Depicker et al., 1985; , McKnight et al., 1987; , De Block and Debrouwer, 1991), site-specific recombination (Dale and Ow, 1991; , Russell et al., 1992), transposition (Goldsbrough et al., 1993; , Gorbunova and Levy, 2000; , Charng et al., 2008), chloroplast transformation (Heifetz, 2000), and positive selection (Joersbo and Okkels, 1996; , Haldrup et al., 1998; , Joersbo et al., 1998). More recently, more scientific researchers have become involved in transgenic plant studies. These sceintists have progressed in developing transgene constructs without antibiotic- or herbicide-resistance selectable marker genes. For instance, Chan and his co-workers (ABRC, Academia Sinica) used the ferredoxin-like protein (pflp) gene, which causes resistance to the soft rot disease caused by *Erwinia carotovora* pathogen, as a selectable marker (Chan et al., 2005) and used the tryptophan synthase beta 1 gene from *Arabidopsis* (AtTSB1) as a native plant selection marker gene (Hsiao et al., 2007; Sanjaya et al., 2008b). Bi-selectable markers have also been used for generating marker-free transgenic plants (Lin et al., 2010). Nevertheless, most of the mentioned-above systems still rely on complicated screening systems.

To date, there is no transgenic system that is suitable for all crops. Each transgenic system has its merits and drawbacks. Most researchers who develop transgenic plants still rely on traditional approaches that use antibiotic- or herbicide-genes as a selectable markers. For long-term development, it is essential to develop a transgenic system approach that does not risk environmental contamination. Toward this goal, we cloned and characterized the GLUCOSE INHIBITION of ROOT ELONGATION 1 (GIR1) gene, which is also known as the cellulose synthase-interactive protein 1, AtCSI1 (Gu et al., 2010), from Arabidopsis. In addition to short swollen roots in the presence of sugars, the Atgir1 mutant showed a severe sterility and a bushy phenotypes in mature plants; moreover, its promoter was wound-inducible. Although this gene was recently cloned and shown to affect cell wall biosynthesis and to interact with cellulose synthase (Gu et al., 2010), its function remains unknown, particularly its wound-inducible aspect. Because the sterility and bushy phenotypes are useful for some agricultural crops that provide vegetative tissues, rather than seeds, for food resources, we thus attempted to clone and manipulate the expression of this gene from broccoli (*Brassica oleracea*). Furthermore, we investigated the possible application of its wound-inducible promoter in transgenic plants. Our results indicated that RNA interference (RNAi) of broccoli GIR1 (BoGIR1) expression alters inflorescence and flower organ development. Interestingly, BoGIR1 promoter activity can be wound-inducible in transgenic broccoli plants expressing pBoGIR1::GUS within 30 min. Similarly, such wound-inducible expression was observed in rice and *Arabidopsis* transgenic plants heterologously expressing pBoGIR1::GUS. Thus, pBoGIR1::GUS can be used in a variety of plant species, including monocots and dicots, and can serve as a substitute for antibiotic - and herbicide-resistance genes for the development of genetically modified crops.

SUMMARY OF THE INVENTION

This invention discloses the use of a wound-inducible promoter of the broccoli (*Brassica oleracea* var. *italica*) GLUCOSE INHIBITION of ROOT ELONGATION1 (GIR1) gene fused to β-glucuronidase (GUS, pBoGIR1::GUS) as a selectable marker. Transgenic broccoli plants expressing pBoGIR1::GUS appear blue in planta at wounded regions after GUS staining for 30 min. Similarly, the blue color is visible in transgenic *Arabidopsis* and rice plants expressing pBoGIR1::GUS at wounded areas after GUS staining for 2 h, indicating that this promoter is wound-inducible in both dicots and monocots. GUS staining is very rapid and the partial wounding is a nondestructive method that does not affect further plant growth and development. Thus, the disclosed pBoGIR1::GUS could serve as an effective substitute for antibiotic- and herbicide-resistance genes in the generation of genetically modified crops.

BRIEF DESCRIPTION OF THE FIGURES

FIG. 1. Gene structure, amino acid alignment, and phylogenetic analysis of BoGIR1 and its homologs among plant species.
  A. Full-length genomic DNA and cDNA of BoGIR1.
  B. Predicted protein structure of BoGIR1.

C. C2-domain sequence alignment of BoGIR1 and its homologs among plant species. Asterisks represent fully conserved residue and dots stand for strongly conserved residues.

D. Phylogenetic analysis of BoGIR1 and its homologs among plant species. The scale value of 0.1 indicates 0.1 amino acid substitutions per site.

FIG. 2. RNAi transgene and analysis of RNAi transgenic plants.

A. The RNAi transgene construct derived from pFGC5941 dsRNA vector (ABRC stock number CD3-447). OCS, octopine synthase; CHSA, chalcone synthase A gene; Omega, TMV omega leader sequences; p35S, a CaMV 35S promoter; MAS, manopine synthase; BAR, a basta resistance gene for plant selection; LB and RB, left and right borders.

B. Southern blot analysis of broccoli RNAi transgenic broccoli plants. Genomic DNA was extracted from the leaves of 7-week-old transgenic plants and each of 30 µg of DNA was subjected to restriction enzyme digestion by Bam HI or Hind III. The blot was hybridized with a 32P-labelled BAR gene as a probe.

C and D. Northern blot (C) and reverse transcriptase (RT-) PCR (D) analyses of BoGIR1 transcripts from wild-type and RNAi transgenic broccoli plants. Total RNA was extracted from the leaves of broccoli transgenic plants. For Northern blots, 35 µg of total RNA was loaded into each lane. The rRNA and BoACTIN probes were used as internal loading controls for Northern blots and RT-PCR analyses, respectively.

FIG. 3. Phenotypic comparison of wild-type and RNAi transgenic plants in broccoli.

A and B, The inflorescence of wild-type plants showing top (A) and side (B) views.

C and D, The inflorescence of the RNAi-8 transgenic plant showing top (C) and side (D) views.

E, Flowering of wild-type (at left) and RNAi transgenic (at right) plants.

F and G, Comparison of pollen phenotypes between wild-type (H) and RNAi transgenic (I and J) plants.

K, Comparison of flower shoots between wild-type (on the top) and RNAi (on the bottom) transgenic plants.

FIG. 4. Tissue-specific and wound-inducible expression of BoGIR1 in broccoli.

A to C, Transgenic broccoli plants grown in soil for three months were subjected to GUS staining in the anther of an opening flower (A), the roots (B), and a wounded leaf (C). (A) to (C) were subjected to fixation and ethanol washes during GUS staining.

D and E, The main veins of broccoli leaves were wounded and immediately treated with the GUS substrate X-Gluc for 2 h in wild-type (D) or RNAi transgenic (E) plants. The inset in (E) shows the petiole. The arrows indicate the wounded regions.

FIG. 5. Heterologous expression of pBoGIR1::GUS in *Arabidopsis* transgenic plants.

A and B, *Arabidopsis* transgenic plants expressing pBoGIR1::GUS were grown in soil for two weeks and then subjected to GUS staining (A). (B) is the close-up view of (A).

C to E, *Arabidopsis* transgenic plants expressing pBoGIR1::GUS were grown in soil for eight weeks and then subjected to GUS staining of the inflorescence (C), wounded cauline leaf (D) and mature siliques (E). Samples in (A) to (E) were subjected to fixation and ethanol washes during GUS staining.

F to H, *Arabidopsis* wild-type (F) and transgenic (G and H) plants expressing pBoGIR1::GUS were grown in soil for four weeks and then the petioles were wounded and treated with the GUS substrate X-Gluc for two (G) and five (F and H) hours.

FIG. 6. Heterologous expression of pBoGIR1::GUS in rice transgenic plants.

A and B, wild-type rice (TNG67) (A) and transgenic plant (B) expressing pBoGIR1::GUS were grown in soil for 52 days; the petioles were wounded (dashed square in red) and subjected to X-Gluc treatment.

FIG. 7. Deletion assay of BoGIR1 promoter. The BoGIR1 promoter with 1.8 kb upstream of the ATG start codon was deleted at 300 bp intervals by PCR amplification. These fragmented promoters were subsequently transformed into *Arabidopsis* using an *Agrobacterium*-mediated floral-dip method. The cauline leaves of three independent transgenic plants harboring each promoter fragment, which had been grown in soil for 42 days, were stained with GUS substrate (X-Gluc), and one of the representative cauline leaves is shown together with its corresponding promoter.

FIG. 8. The Promoter sequences of BoGIR1 (designated as SEQ ID NO: 1) and its putative wound-inducible cis-acting elements. Cis-acting elements were searched by PlantCARE (accessed via PlantCARE website on or about Aug. 11, 2011) and PLACE (accessed via PLACE website on or about Aug. 11, 2011). T/G-boxes are shown in blue with an underline and the W-box sequence of TACGTG is red surrounded by a box.

DETAILED DESCRIPTION OF THE INVENTION

Plant Materials and Methods
Plant Materials and Growth Conditions

The plants used in this study were commercial F1 hybrid broccoli (*Brassica Oleracea* var. *italica*) Green King (Known-You Seed Co. Ltd., Kaohsiung, Taiwan), Columbia-ecotype *Arabidopsis* (*Arabidopsis thaliana*), and rice (*Oryza saliva* TNG67). For broccoli and rice, seeds were sown in soil and grown in a walk-in growth chamber under long-day conditions with a 16-h light/8-h dark cycle at 22° C. (for broccoli) or 28° C. (for rice) and a light intensity of approximately 80 µE/sm$^2$. The growth conditions for *Arabidopsis* have been described previously (Lin et al., 2007)

Cloning of Broccoli GIR1 Gene

For the cloning of the broccoli GIR1 gene, namely BoGIR1 degenerate primers were designed according to the nucleotide alignment of AtGIR1 (At2g22130) with its homologs from rice (*Oryza sativa* Japonica, AK105686), maize (*Zea mays* AY104909), and chickpea (*Cicer aritinum* AJ630655). The ~1.2 kb At2g22130 was later replaced by At2g22125 in the TAIR database (accessed via *Arabidopsis* website on or about Aug. 11, 2011). Two degenerate primer pairs were used in this study, including GIR1-F1(forward) 5'-ATWCCH-CAYCTDGTHACATC-3' (SEQ ID NO: 2); GIR1-R1 (reverse) 5'-GACCAYTGRAAYTCWATYTC-3' (SEQ ID NO: 3); GIR1-F2 5'-WTCTKCTYAGRCAAGCWTGG-3' (SEQ ID NO: 4); and GIR1-R2 5'-CKRTCGATYTG-GATYGTYAC-3' (SEQ ID NO: 5). The primer pair, GIR1-F1 and GIR1-R1, was first used to amplify a partial fragment of the BoGIR1 gene through PCR amplification. The resulting PCR product was then used as a template for a second PCR amplification using the primer pair GIR1-F2 and GIR1-R2. The second PCR product showed a clear band shift relative to the first PCR product on a gel. This second PCR product, with an expected size of ~414 bp, was cloned into the pGEM-T Easy vector (Promega, Madison, WI, USA) for sequencing and was confirmed as a putative fragment of BoGIR1 by TAIR BLAST analysis (accessed via Arabidoposis website on or about Aug. 11, 2011). Subsequently, the sequenced fragment was used to design BoGIR1 gene-specific primers to obtain the full-length cDNA of broccoli GIR1 (GenBank accession no. JN587274) via Rapid Amplification of cDNA Ends (RACE; Clontech, Catalog no. 634914 or K1811-1). For promoter cloning, PCR-based DNA walking was performed according to the manufacturer's instructions (Clontech, BD GenomeWalker Universal Kit, Cat. no. 638904). The resulting PCR product was cloned into the pGEM T-Easy vector for sequencing. The confirmed promoter fragment was ~1.8 kb.

Transgene Constructs and Transgenic Plant Isolation

The transgene construct of double-strand (ds) RNA interference (RNAi) was generated by PCR amplification of a BoGIR1 partial fragment of 428 bp (5647 through 6074 bp of full-length BoGIR1 cDNA) at sense and antisense strands, and was subsequently ligated into a pFGCS5941 dsRNAi vector, which was driven by a 35S promoter and contained a BAR selectable gene. The vector pFGCS5941 for dsRNAi was obtained from the ABRC (stock no. CD3-447) (accessed via *Arabidoposis* website on or about Aug. 11, 2011). For tissue-specific expression analysis, a transgene composed of the BoGIR1 promoter (1.8 kb) fused to a β-glucuronidase (GUS) coding region (pBoGIR1::GUS) was constructed. For transformation and transgenic plant isolation, cotyledons and hypocotyls of broccoli seedlings grown in vitro on MS basal medium for 3-4 days were cut into pieces as explants and co-cultured with *Agrobacterium*-harboring dsRNAi transgene plasmids. The wash and subculture of explants and transgenic plant screening and isolation were according to the protocol described previously (Chen et al., 2008). We obtained approximately 30 Independent transgenic plants from RNAi and approximately 17 from pBoGIR1::GUS constructs. At least three of these independent lines of each were used for further study. For heterologous expression of pBoGIR1::GUS in *Arabidopsis* and rice, transformation, screening and transgenic plant isolation were performed according to the previously described protocols (Lin et al., 2007; , Sallaud et al., 2003).

Southern and Northern Blots and Reverse Transcriptase (RT)-PCR

For Southern blot analysis, genomic DNA was extracted from the leaves of RNAi transgenic broccoli plants grown in soil for 50 days. BamHI and HindIII restriction enzymes were used to digest 30 μg of the purified DAN, and then the digested DNA was subjected to electrophoresis for size fragmentation. Subsequently, the blotting, hybridization, and wash essentially followed the previously described protocol (Dellaporta et al., 1983). The PCR -based $^{32}$P-labeled Bar gene was used as the hybridization probe. For Northern blot analysis, total RNA was extracted from the young leaves of wild-type and RNAi transgenic broccoli plants grown in soil for 60 days. Thirty-five micrograms of total RNA from each genotype was used and separated on a 1% agarose gel; the subsequent blotting steps were performed according to the previously described protocol (Wadsworth et al., 1988). A less conserved region of BoGIR1 (coding sequences from 2565 to 3636 bp) was $^{32}$P-labeled by PCR and used as a probe for the Northern blot. For RT-PCR, six μg of total RNA obtained from the mentioned-above samples was mixed with 1 μg of oligo(dT) primer (Invitrogen, USA), heated at 70° C. for 5 min, and immediately chilled on ice. The RNA was then subjected to reverse transcription with reverse transcriptase at 37° C. for 1 h. The resulting complementary DNA (cDNA) was used as a template for PCR. The following primer pair was used to amplify the full-length BoGIR1 coding region of 6454 bp: BoGIR1-F 5'-CCCGGGATGGCAAGTGCACT-TGGATGGAG-3'(SEQ ID NO: 6) and BoGIR1-R 5'-CCCGGGTTACTTGTTGGACCACTGAAATTC-3' (SEQ ID NO: 7. The broccoli ACTIN gene of 1242 bp was used as an internal control using the following primer pair: BoACTIN-F 5'-CCAGATCATGTTCGAGACCTTC-3' (SEQ ID NO: 8) and BoACTIN-R 5'-GAACCTCTCATTGC-CAATGGTG-3' (SEQ ID NO: 9).

GUS staining

The detached plant organs, such as flowers, roots, and wounded leaves, from broccoli, *Arabidopsis* or rice were vacuum-infiltrated for 30 seconds and incubated for 45 min at room temperature in a fixative solution composed of 0.3% formaldehyde, 10 mM MES [2-(N-morpholino)ethane-sulfonic acid monohydrate] (pH 5.6), 0.3 M mannitol, and 2 mM DTT (dithiothreitol). The fixed samples were then washed several times in 50 mM sodium phosphate buffer (pH 7.0) before being immersed into a GUS substrate solution containing 1 mM 5-bromo-4-chloro-3-indolyl β-D-glucuronide (X-Gluc, Sigma, Cat. no. B 0522), 50 mM phosphate buffer (pH 7.0), 0.5 mM potassium ferricyanide, 0.5 mM potassium ferrocyanide, and 5 mM DTT (Yang et al., 1995). The substrate-treated samples were incubated at 37° C. for a time period dependent on the experimental design. For in planta GUS staining, a 1% agarose gel that contained the X-Gluc solution was placed directly on the wounded regions of plant tissues for the time periods listed in the text. At least three to five independent lines were tested for GUS staining and all of them showed consistent staining results.

Methods for Scanning Electron Microscopy (SEM)

The anthers of opening flowers of wild-type and RNAi transgenic broccoli plants were loaded on stubs, frozen by liquid nitrogen slush and incubated in a sample preparation chamber at −160° C. for 5 min. Subsequently, the temperature was lowered to −85° C. and the samples were sublimed for 10-15 min. After coating with Au at −130° C., the samples were transferred to a cryo stage in a SEM chamber and observed at −160° C. in a SEM (FEI Quanta 200 SEM/Quorum Cryo System PP2000TR FEI).

Results

Molecular Cloning of Broccoli GIR1 and Analysis of its Structure

Our previous study (data not shown) indicated that plasma membrane (PM)- and endoplasmic reticulum (ER)-associated AtGIR1, also known as cellulose synthase-interactive protein 1, AtCSI1 (Gu et al., 2010), plays a vital role in root and flower development through glucose signaling to the homeostasis of cell wall and lipid metabolism in *Arabidopsis*. The mature plants of the Atgir1 mutant show more flower shoots than the wild type and form a bushy shape. To investigate whether the Atgir1 mutant phenotypes can be observed in broccoli, which is also a member of *Brassica* family, we isolated GIR1 in broccoli with degenerate primers and Rapid Amplification of cDNA Ends (RACE). As shown in FIG. 1, the BoGIR1 genomic DNA consisted of 7844 bp that included seven exons and six introns. The full-length cDNA of BoGIR1 consisted of 6853 bp that included a 209-bp 5' untranslated region (UTR), a 6450-bp coding region, and a 194-bp 3' UTR (FIG. 1A). This gene encoded a putative protein of 2149 amino acids and a predicted molecular mass of 230,7 kD. This protein contained 18 Armadillo (ARM) repeats and a C2 domain of amino acids 2030 to 2126 at its C-terminal end (FIG. 1B).

The amino acid alignment of the C2 domain of BoGIR1 with its orthologs among plant species indicated that the BoGIR1 C2 domain had a higher identity to dicots than to monocots. For instance, the BoGIR1 C2 domain had 98% identity to AtGIR1 and 94 to 90% identity to other dicots, such as castor (*Ricinus communis*), poplar (*Populus trichompa*), common grape vine (*Vitis vinifera*), and chickpea (*Cicer arietinum*). However, the BoGIR1 C2 domain had 80% identity to GIR1 in rice (*Oryza saliva* Japonica Group) and 54% identity to GIR1 in maize (*Zea mays*) (FIG. 1C). Phylogenetic analysis further revealed that BoGIR1 was closest to AtGIR1, with a 95% identity and formed a clade close to other dicots. However, BoGIR1 was separated from rice, a monocot. These data suggest a possible GIR1 sequence divergence when dicots and monocots diverged. Two AtGIR1 homologs, At1g44120 and At1g77460, formed another clade distant from BoGIR1 (FIG. 1D). These two proteins contained different numbers of ARM repeats from AtGIR1, and their T-DNA-knockdown single and double mutants did not show any visible mutant phenotype (data not shown). These results suggest that these two homologs might have a different function than AtGIR1.

Generation of BoGIR1 RNAi Transgenic Plants

To date, no sequence database or T-DNA insertion seed pools have been available for broccoli. To investigate the effect of the BoGIR1 gene on broccoli growth and development, an RNA interference (RNAi) transgene was constructed. This transgene was constructed in a pFGCS5941 dsRNAi vector and contained a 428 bp (5647 through 6074 bp in the full-length cDNA) of BoGIR1 sense and antisense fragments inserted into the 5' and 3' terminal ends of the chalcone synthase A intron (FIG. 2A). Subsequently, the transgene was transformed into broccoli plants through *Agrobacterium*-mediated transformation. More than 30 putative transgenic plants (T1) were isolated on the basis of herbicide selection. Of these, three independent lines, designated RNAi-5, RNAi-8, and RNAi-9, were randomly chosen for further study. Southern blot analysis indicated that each of these three RNAi transgenic lines contained at least two copies of the transgene in their genomes (FIG. 2B). Furthermore, Northern blot study confirmed that these transgenic broccoli plants had a considerable reduction of BoGIR1 transcript compared to the wild-type control (FIG. 2C). The significant reduction of BoGIR1 transcripts was also confirmed by RT-PCR amplification of the full-length BoGIR1 coding region (FIG. 2D). These data indicate that RNA interference efficiently knocked down the endogenous BoGIR1 expression in this study.

RNA Interference of BoGIR1 Expression Alters Flower Development in Broccoli

The comparison of the RNAi transgenic plants with the wild-type control revealed that the inflorescence of these RNAi transgenic plants possessed more compact flower clusters (curds) than wild-type plants (FIGS. 3A and B vs. 3C and D). While wild-type inflorescence completely flowering, approximately half of florets in the RNAi transgenic plant remained unopened and greening (FIG. 3E). Florets of RNAi transgenic plant were smaller and lost fertility as compared to wild-type plants. The severe phenotype observed in RNAi transgenic plants also included protruding stigmas and less petal exposure during flowering (FIGS. 3E and F). The pollens of RNAi transgenic plants showed markedly deformed shapes (FIG. 3I) and led to sterility. This genetic material could be maintained by crossing female RNAi transgenic plants with male wild-type plants. This finding indicates that the sterility was primarily due to the failure of male function. Some transgenic plants produced compact inflorescence with mild sterility; these showed mainly a flowering phenotype with a substantial level of aborted pollens (FIGS. 3G and J). Detailed analysis of inflorescence showed that the total numbers of florets and flower shoots in RNAi transgenic plants were, respectively, ~3-fold and 2-fold higher than in wild-type plants (n≥3). One of the examples (FIG. 3K) showed that the total numbers of florets and flower shoots in transgenic plant RNAi-8 of 110 and 4243, respectively, and 59 and 1283, respectively, in wild-type plants. Taken together, these data suggested that RNA interference of BoGIR1 expression alters inflorescence and flower organ development.

Tissue-specific Expression of BoGIR1 in Broccoli and *Arabidopsis*

To further elucidate the spatial and temporal expression pattered of BoGIR1, transgenic broccoli plants harboring a transgene composed of a BoGIR1 promoter (1.8-kb) fused to β-Glucuronidase (GUS), named pBoGIR1::GUS, were generated. A total of 17 independent transgenic plants were isolated on the basis of herbicide selection. Three independent homozygous transgenic plants were used for further study. As shown in FIG. 4, the GUS signal was predominantly present in mature opened anthers, pollens (FIG. 4A), and roots (FIG. 4B). The wounded leaf also showed apparent GUS staining (FIG. 4C). Because the BoGIR1 promoter appeared to be strongly wound-inducible (FIG. 4C), we directly wounded the main veins of leaves and petioles and immediately added X-Gluc to the wounded areas. Surprisingly, the GUS signal was initially visible 30 min after treatment and it became more pronounced after 2 h (FIGS. 4D and E). For comparison with AtGIR1 expression patterns, the pBoGIR1::GUS transgene was also heterologously transformed into *Arabidopsis*. As shown in FIG. 5, the GUS staining signal predominantly appeared in roots (FIG. 5A), seedling stipules (FIG. 5B), pollens, and the junctions of pedicels and young developing siliques (FIG. 5C). The staining signal was also observed in wounded cauline leaves (FIG. 5D) and in opened mature siliques (FIG. 5E). This expression pattern was largely reminiscent of the pAtGIR1::GUS expression in transgenic *Arabidopsis* plants (data not shown). Similarly, the heterologous expression of pBoGIR1::GUS in rice showed visible GUS staining in the petiole of transgenic rice after 2 h of X-Gluc treatment in planta (FIG. 6). These data suggest that the BoGIR1 promoter directs the spatial and temporal expression in transgenic broccoli, *Arabidopsis* and rice transgenic plants, and is strongly wound-inducible in planta.

Promoter Analysis of BoGIR1 Gene and its Putative Wound-inducible Elements

To further pinpoint the location of the wound-inducible cis-acting elements, the BoGIR1 promoter of 1.8 kb was deleted at 300 bp intervals and fused with the GUS coding region. These pBoGIR1::GUS transgenes were then transformed into *Arabidopsis* plants. The resulting transgenic plants were examined by GUS staining. As shown in FIG. 7, transgenic *Arabidopsis* plants expressing pBoGIR1::GUS showed no GUS staining signal when expressing the BoGIR1 promoter region below 300 bp. However, transgenic Arabidopsis plants expressing BoGIR1 promoter regions above 300 bp showed wound-inducible GUS staining signal, which suggested that the wound-inducible elements located more than 300 bp upstream of the ATG start codon. Consistent with this result, promoter sequence analysis by PlantCARE (accessed via PlantCARE website on or about Aug. 11, 2011) or PLANCE (accessed via PLANCE website on or about Aug. 11, 2011) further indicated that the BoGIR1 promoter contained five W boxes (TTGACC/T) and one T/G box (TACGTG) (FIG. 8). The locations of these elements were more than 300 bp upstream of the ATG start codon and these elements had previously been reported to have a wound-inducible function (Boter et al., 2004; Wu et al., 2009). Thus, these data demonstrated that 600 bp of the BoGIR1 promoter is sufficiently to lead to wound-inducible signals.

Discussion

The plant cell wall is the most abundant carbon resource in higher plants. It has been believed that plant cell wall is not a rigid and static structure; instead, it is a dynamic and responsive wall that acts as part of a continuum with the plasma membrane and cytoskeleton (Humphrey, 2007). The plant cell wall is a complex materials composed predominantly of a polysaccharide network that includes cellulose, hemicellulose, and pectin along with a small but important fraction of functional proteins. Cellulose exists as microfibrils consisting of parallel β-1,4-linked glucan chains that are held together laterally by hydrogen bonds. In vascular plants, cellulose is synthesized by a hexameric cellulose synthase (CESA) complex, which resides in the plasma membrane (Somerville, 2006).

The CESA complex is though to include the major enzyme proteins that are responsible for the production of microfibrils. Although additional cellulose-deficient mutants, including cobra, sos5, fei1fei2, and prc1, have been identified, none of these genes yet have a defined function in cellulose biosynthesis (Arioli et al., 1998; , Fagard et al., 2000; , Schindelman et al., 2001; , Shi et al., 2003; Roudier et al., 2005). Further, there is no report that the CESA complex has any interacting proteins that are involved in cellulose biosynthesis. Until recently, GIR1 (also known as CSI1) had been the only identified protein to directly interact with CESA1, 3, and 6 (Gu et al., 2010 and our unpublished data). A defect in GIR1 causes the reduction of cellulose biosynthesis and affects the distribution and movement of CESA complexes in the plasma membrane (Gu et al., 2010). In addition, the gir1/csi1 mutant shows phenotypes of short roots and sterility. Although GIR1 plays important roles in mediating plant growth and development, its function remains obscure. It has been proposed that GIR1 might guide the CESA complex along the microtubules during cellulose biosynthesis. The microtubule-associated protein (MAP) might be necessary for this two-component association. Alternatively, GIR1/CSI1 may be responsible for the delivery of the CESA complex from the Golgi bodies into the plasma membrane (Endler and Persson, 2011).

The gir1 mutant displayed severe sterility and a bushy shape at the late developmental stage. These phenotypes are useful for crops that produce inflorescences rather than seeds as food resources. Thus, we used RNAi interference to knockdown broccoli BoGIR1 gene function. We found that transgenic broccoli plants expressing the dsRNAi BoGIR1 construct exhibited compact inflorescences with more flower shoots and florets, and severe sterility (FIG. 3). These phenotypes are similar to the Atgir1 mutant of *Arabidopsis*. Although the *Arabidopsis* Atgir1 mutant displays short swollen roots in the presence of sugars in the medium (Gu et al., 2010 and our unpublished data), this phenotype was not observed in the RNAi transgenic broccoli plants. This discrepancy is likely because the Atgir1 mutant is a knockout mutant, whereas the RNAi transgenic plants are knockdown mutants. The latter contained partial BoGIR1 activity and sufficiently maintained the root phenotype, but its expression was not adequate for normal inflorescence growth.

In addition to its significantly physiological role in root elongation and inflorescence development, GIR1 also revealed a strong wound-inducible promoter. Currently, there is no report regarding the wound-inducible activity of GIR1 in broccoli and *Arabidopsis* or the promoter sequences in broccoli BoGIR1. Further promoter deletion and cis-acting element analysis of the BoGIR1 promoter revealed that this promoter contained 5 W-boxes (TTGACC/T) and one T/G-box (TACGTG) within the region 1.8 kb upstream of the ATG start codon. These two types of cis-acting elements have been reported to have wound-inducible function (Boter et al., 2004; , Wu et al., 2009). *Arabidopsis* and broccoli transgenic plants expressing their native GIR1 promoters fused with β-glucuronidase (pGIR1::GUS) express GUS at any wounded area, in addition to specific tissues such as pollens and roots. When these two plant species are compared, the broccoli promoter has a much stronger wound-inducible activity than that of *Arabidopsis*. We observed that the GUS signal was visible 30 min after wounding in transgenic broccoli plants and wounding signal can be observed within 2 h in transgenic *Arabidopsis* and rice plants heterologously expressing pBoGIR1::GUS. Thus, the wound-inducible promoter pBoGIR1 fused to GUS has the potential to replace antibiotic- or herbicide-resistance genes as a selectable marker. The several advantages of this technique are the following.

1. This BoGIR1 promoter is derived from a plant gene. Although the β-glucuronidase (GUS) gene is originally derived from a bacterium, this protein is very stable and shows no toxicity in plants. Thus, the transgenic plants expressing pBoGIR1::GUS will not cause any environmental contamination.
2. We observed that the broccoli BoGIR1 promoter has a much stronger wounding response than the *Arabidopsis* AtGIR1 promoter. BoGIR1 also possesses a wounding response when it is heterologously expressed in the monocot rice (FIG. 6). This finding indicates that this promoter can be used in a wide range of plant species, including monocots and dicots.
3. The blue color as a selectable marker is simple and convenient and is even feasible in seedlings grown in sterile vials or bottles. Application of a droplet of the GUS substrate X-Gluc to a small wound on a leaf will generate the blue colored product within a short time period (less than 2 h). The transgenic plants selected on the basis of their blue color may grow normally thereafter and do not need to go through complicated selection to exclude the antibiotic/or herbicide genes.
4. This method will become useful for the important crops for which antibiotic and herbicide selections are not easily used to establish transgenic system.
5. The pBoGIR1 promoter fused to anti-insect genes also has a great potential to generate transgenic plants that are protected from insect infection. Once the transgenic plants are wounded by insects, the anti-insect transgenic gene would be induced and eventually lead to insect resistance.

While embodiments of the products, methods, and systems have been shown and described in this specification, it will be apparent to those skilled in the art that many more modifications and variations are possible without departing from the inventive concepts herein. The invention, therefore, is not to be restricted or limited except in the spirit of the following claims.

References

Arioli T, Peng L, Betzner A S, Burm J, Wittke W, Herth W, Camilleri C, Höfte H, Plazinski J. Birch R et al. (1998). Molecular analysis of cellulose biosynthesis in *Arabidopsis*. Science 279: 717-720.

Boter M, Ruíz-Rivero O, Abdeen A, and Prat S. (2004). Conserved MYC transcription factors play a key role in jasmonate signaling both in tomato and *Arabidopsis*. Genes and Development 18: 1577-1591.

Chan Y L, Sanjaya, Lin K H, Liao L J, Chen W H, and Chan M T. (2005). Gene stacking in *Phalaenopsis* orchid enhances dual tolerance to pathogen attack. Transgenic Research 14: 279-288.

Charng Y C, Li K T, Tai H K, Lin N S, Tu J. (2008). An inducible transposon system to terminate the function of a selectable marker in transgenic plants. Mol Breed 21: 359-368.

Chen L F O, Lin C H, Kelkar S M, Chang Y M, and Shaw J F. (2008). Transgenic broccoli (*Brassica oleracea* var. *italica*) with antisense chlorophyllase (BoCLH1) delays postharvest yellowing. Plant Science 174: 25-31.

Dale E C, Ow D W. (1991). Gene transfer with subsequent removal of the selection gene from the host genome. Proc Natl Acad Sci (USA) 88: 10558-10562.

Dellaporta S, Woody J, Hicks B. (1983). A plant DNA minipreparation: version II. Plant Mol Biol Rep 4: 19-21.

Depicker A, Herman L, Jacobs S, Schel J, van Montagu M. (1985). Frequencies of simultaneous transformation with different T-DNA and their relevance to the *Agrobacterium* plant cell interaction. Mol Gel Genet 201: 477-484.

De Block M, Debrouwer D. (1991). Two T-DNA co-transformed into *Brassica napus* by a double *Agrobacterium* infection are mainly integrated at the same locus. Theor Appl Genet 82: 257-263.

Endler A, Persson S. (2011). Cellulose synthases and synthesis in *Arabidopsis*. Mol Plant 4: 199-211.

Fagard M, Dsnos T, Desprez T, Goubet F, Refregier G, Mouille G, McCann M, Rayon C, Vernhettes S, Höfte H. (2000). PROCUSTE1 encodes a cellulose synthase required for normal cell elongation specifically in roots and dark-grown hypocotyls of *Arabidopsis*. Plant Cell 12: 2409-2424.

Goldsbrough A P, Lastrella C N, Yoder J I. (1993). Transposition mediated re-positioning and subsequent elimination of marker genes from transgenic tomato. Biotech 11: 1286-1292.

Gorbunova V, Levy A A. (2000). Analysis of extrachromosomal Ac/Ds transposable elements. Genetics 155: 349-359.

Gu Y, Kaplinsky N, Bringmann M, Cobb A, Carroll A, Sampathkumar A, Baskin T, Persson S, Somerville C R. (2010). Identification of a cellulose synthase-associated protein required for cellulose biosynthesis. Proc Natl Acad Sci (USA) 107: 12866-12871.

Haldrup A, Petersen S G, Okkels F T. (1998). The xylose isomerase gene from *Thermoanaerobacterium thermosulfurogenes* allows effective selection of transgenic plant cells using D-xylose as the selection agent. Plant Mol Biol 37: 287-296.

Heifetz P B. (2000). Genetic engineering of the chloroplast. Biochimie 82: 655-666.

Hsiao P, Sanjaya, Su R C, da Silva J A T and Chan M T. (2007). Plant native tryptophan synthase beta 1 gene act as a non-antibiotic selection marker for plant transformation. Planta 225: 897-906.

Humphrey T V, Bonetta D T, Goring D J. (2007). Sentinels at the wall: Cell wall receptors and sensors. New Phytol 176: 7-21.

Joersbo M, Okkels F T. (1996). A novel principle for selection of transgenic plant cells: positive selection. Plant Cell Reports 16: 219-221.

Joersbo M, Donaldson I, Kreberg J, Petersen S G, Brundstedt J, Okkels F T. (1998). Analysis of mannose selection used for transformation of sugar beet. Mol Breed 4:111-117.

Lin C Y, Ku H M, Tan C W, Yeh S D and Jan F J. (2011). Construction of binary vectors with bi-selectable markers for generating marker-free transgenic plants. Botanical Studies (in press).

Lin P C, Hwang S G, Endo A, Okamoto M, Koshiba T, and Cheng W H. (2007). Ectopic expression of ABSCISIC ACID 2/GLUCOSE INSENSITIVE 1 in *Arabidopsis* promotes seed dormancy and stress tolerance. Plant Physiol 143: 745-758.

McKnight T D, Lillis M T, Simpson R B. (1987). Segregation of genes transferred to one plant cell from two separate *Agrobacterium* strain. Plant Mol Biol 8: 439-445.

Roudier F, Fernandez A G, Fujita M, Himmelspach R, Borner G H, Schindelman G, Song S, Baskin T I, Dupree P, Wasteneys G O, Benfey P N. (2005). COBRA, an *Arabidopsis* extracellular glycosy-phosphatidyl inositol-anchored protein, specifically controls highly anisotropic expansion through its involvement in cellulose microfibril orientation. Plant Cell 17: 1749-1763.

Russell S H, Hoopes J L, Odell J T. (1992). Directed excision of a transgene from the plant genome. Mol Gen Genet 234: 49-59.

Sallaud C, Meynard D, van Boxtel J, Gay C, Bés M, Brizard J P, Larmande P, Ortega D, Raynal M, Portefaix M, Ouwerkerk P B F, Rueb S, Delseny M, and Guiderdoni E. (2003). Highly efficient production and characterization of T-DNA plants for rice (*Oryza saliva* L.) functional genomics. Theor Appl Genet 106: 1396-1408.

Sanjaya, Hsiao P, Su R C, Ko S S, Tong C G, Yang R Y and Chan M T. (2008a). Overexpression of *Arabidopsis thaliana* tryptophan synthase beta 1 (AtTSB1) in *Arabidopsis* and tomato confers tolerance to cadmium stress. Plant, Cell and Environment 31:1074-1085.

Sanjaya and Chan M T. (2008b). Non-antibiotic selection marker genes in plant transformation: present and future prospects. Current Topics in Plant Biology 9: 69-78.

Schindelman G, Morikami A, Jung J, Baskin T I, Carpita N C, Derbyshire P, McCann M C, Benfey P N. (2001). COBRA encodes a putatiave GPI-anchored protein, which is polarly localized and necessary for oriented cell expansion in *Arabidopsis*. Genes Dev 15: 1115-1127.

Shi H, Kim Y, Guo Y, Stevenson B, Zhu J K. (2003). The *Arabidopsis* SOS5 locus encodes a putative cell surface adhension protein and is required for normal cell expansion. Plant Cell 15: 19-32.

Somerville C. 2006. Cellulose synthesis in higher plants. Annu Rev Cell Dev Biol 22: 53-78.

Wadsworth G J, Redinbaugh M G, Scandalios J G. (1988). A procedure for the small-scale isolation of plant RNA suitable for RNA blot analysis. Anal Biochem 172: 279-283.

Wu X F, Wang C L, Xie E B, Gao Y, Fan Y L, Liu P Q, and Zhao K J. (2009). Molecular cloning and characterization of the promoter for the multiple stress-inducible gene BjCHI1 from *Brassica juncea*. Planta 229: 1231-1242.

Yang P, Taoka K, Nakayama T, and Iwabuchi M. (1995). Structural and functional characterization of two wheat histone H2B promoters. Plant Mol Biol 28: 155-172.

What is claimed is:

1. A vector comprising a broccoli wound-inducible promoter comprising the nucleotide sequence of SEQ ID NO: 1 and a heterologous nucleotide sequence.

2. The vector of claim 1, further comprising a cis-acting element selected from the group consisting of TTGACA, AACTGA, TACGTG, AGTCAA, TATA, and ATG.

3. A transgenic plant comprising the vector of claim 1.

4. A transgenic plant cell comprising the vector of claim 1.

5. The transgenic plant of claim 3, wherein the transgenic plant is broccoli.

6. The transgenic plant cell of claim 4, wherein the transgenic plant cell is a broccoli cell.

7. The transgenic plant of claim 3, wherein the transgenic plant is *Arabidopsis*.

8. The transgenic plant cell of claim 4, wherein the transgenic plant cell is an *Arabidopsis* cell.

9. The transgenic plant of claim 3, wherein the transgenic plant is rice.

10. The transgenic plant cell of claim 4, wherein the transgenic plant cell is a rice cell.

11. A vector comprising a broccoli wound-inducible promoter comprising 600 bp of contiguous nucleotide sequence from bases 1284 to 1883 of SEQ ID NO: 1 and a heterologous nucleotide sequence.

12. A vector comprising a broccoli wound-inducible promoter comprising 900 bp of contiguous nucleotide sequence from bases 984 to 1883 of SEQ ID NO: 1 and a heterologous nucleotide sequence.

13. A vector comprising a broccoli wound-inducible promoter comprising 1200 bp of contiguous nucleotide sequence from bases 684 to 1883 of SEQ ID NO: 1 and a heterologous nucleotide sequence.

14. A vector comprising a broccoli wound-inducible promoter comprising 1500 bp of contiguous nucleotide sequence from bases 384 to 1883 of SEQ ID NO: 1 and a heterologous nucleotide sequence.

15. The vector of claim 1, wherein the vector comprises a heterologous selectable marker for generating a transgenic plant cell.

16. The vector of claim 1, wherein the vector comprises a heterologous selectable marker for generating a transgenic plant.

* * * * *

SEQUENCE LISTING

<160> NUMBER OF SEQ ID NOS: 17

<210> SEQ ID NO 1
<211> LENGTH: 1883
<212> TYPE: DNA
<213> ORGANISM: Brassica oleracea

<400> SEQUENCE: 1

| | | | | | |
|---|---|---|---|---|---|
| atatcgtatg | ctttcatgag | catagttgtc | gatagaaaca | aaacatgcgt | cgaagagaga | 60 |
| actttgaatc | tttagtttat | tcccattagc | taggcatgag | gccatgtgct | tctttgctct | 120 |
| cccacgttat | atattttacc | actttgggac | aaaagaactg | ctgtcagttt | tcggacagcg | 180 |
| tagaaagatc | atgtcaagga | aataatttac | atgtgtagga | agccacatat | aaaaaataat | 240 |
| attacatcct | tatccacggg | aagctaattc | gaaatgattg | tgatgttgac | aattgttttt | 300 |
| agtaaatttt | cataatcggt | ttggtggtac | ataccttttac | tatcgccatc | ttaatggact | 360 |
| aatcaatcga | gtttggtaac | taatcaatat | atataggtcc | tataacaact | actacaaatc | 420 |
| taatcatttt | ttttcaacat | aggaagggaa | gaagccggat | agtttggcat | aaagacaata | 480 |
| aaacttagaa | aataaattgt | aaaacaataa | ataaacaaaa | aagtaagatg | tttaattaag | 540 |
| tttgtatatc | tctatttgta | actacataat | taattatatt | ataagcaaat | aagcaaaaat | 600 |
| tagaaaactg | attttaata | gtatgttaac | aataatttga | acaaaaacct | atacattata | 660 |
| attaagttta | tgatatactc | tctttgtttc | caaagattga | tattttagaa | ttttatacaa | 720 |
| tattaaaaa | atatgaaatt | ttgattatca | atatattatt | ttctgtaact | aactatttc | 780 |
| aataagtttt | aaccaatagg | ctttcaataa | acacaaatat | gttttgaaa | tttacaattt | 840 |
| accaataatt | aatatattga | aaatgcaaaa | agtatagttt | tgaaacaata | ttttttaaac | 900 |
| atagattttt | tcggaaagga | gggagtaata | tttaaacgtt | agagtttaag | gttaaaattt | 960 |
| agagtaattt | aattaatatt | gtttaataat | ttttttttt | ttgtgatttt | ttgcctctac | 1020 |
| aattttacg | ataattttaa | atgctattaa | tgaaaatttc | taggagtata | tatctaagtt | 1080 |
| acaaaaaaaa | ggtaggagta | taatattaca | tttgtatcag | ttacgtgttt | tcacttgtat | 1140 |
| aatcagtgaa | ataaatggcc | gattagtcgt | aattagtagt | aaatgaagtc | aatgtctcct | 1200 |
| ctcatttgta | atatacaaaa | tatcgactcg | tttggctaag | ccgatcggag | ctggagccgt | 1260 |
| ttagtaaatc | cagtctctgt | cggtggatag | gcaaagccgg | ctccaatctg | ataacacact | 1320 |
| ctcaccagcc | cacacacagc | tctctctctc | tcccctccgt | tttatactta | tttttaagtc | 1380 |
| aaatttcac | aagaaagaga | atcctctccc | tatctctctc | tctaaactgt | tcgacttctt | 1440 |
| cgcttctctt | ctacgaaaca | atcgaatgca | caactgattc | tgctctctcc | tcctcctcct | 1500 |
| cctccttctc | gccattttct | ctctgaggtt | agttcaattc | ctccatctat | ggacctatct | 1560 |
| tcatgctttt | agtacatcgg | atctcttctg | cgtagactgt | gtaccagaat | cgttgatctc | 1620 |
| agtgagggat | ccgagttttt | gaattagatt | ccatcgcgat | ctgagtccta | catccgaatc | 1680 |
| gataaacttt | cctgatttag | attagctcat | caaatctgga | aagtaaaacg | attcggatcg | 1740 |
| ataaaagagt | aatctattag | ttagtattta | ttaattgcat | ttttagcttc | tgatctgatc | 1800 |
| tcttcttcca | gggggagttg | atactctgac | ggtatattct | cgatagatct | gagtagagaa | 1860 |
| tctttgaagt | gtaacagaaa | aga | | | | 1883 |

<210> SEQ ID NO 2
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 2
atwcchcayc tdgthacatc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
gaccaytgra aytcwatytc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
wtctkctyag rcaagcwtgg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
ckrtcgatyt ggatygtyac                                              20

<210> SEQ ID NO 6
<211> LENGTH: 29
<212> TYPE: DNA
<213> ORGANISM: Artificial Sequence
<220> FEATURE:
<223> OTHER INFORMATION: Synthetic Primer

<400> SEQUENCE: 6
cccgggatgg caagtgcact tggatggag                                    29

<210> SEQ ID NO 7
<211> LENGTH: 30
<212> TYPE: DNA
<213> ORGANISM: Artificial Sequence
<220> FEATURE:
<223> OTHER INFORMATION: Synthetic Primer

<400> SEQUENCE: 7
cccgggttac ttgttggacc actgaaattc                                   30

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
ccagatcatg ttcgagacct tc                                           22
```

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
gaacctctca ttgccaatgg tg                                           22

<210> SEQ ID NO 10
<211> LENGTH: 107
<212> TYPE: PRT
<213> ORGANISM: Brassica oleracea

<400> SEQUENCE: 10

Ala Glu Phe Leu Leu Gln Cys Leu Pro Gly Thr Leu Val Val Thr Ile
1               5                   10                  15

Lys Arg Gly Asn Asn Met Lys Gln Ser Val Gly Asn Pro Ser Val Phe
            20                  25                  30

Cys Lys Ile Thr Leu Gly Asn Thr Pro Pro Arg Gln Thr Ser Val Ile
        35                  40                  45

Ser Thr Gly Pro Asn Pro Glu Trp Asp Glu Ser Leu Ser Trp Ser Phe
    50                  55                  60

Glu Ser Pro Pro Lys Gly Gln Lys Leu His Ile Ser Cys Lys Asn Lys
65                  70                  75                  80

Ser Lys Met Gly Lys Ser Ser Phe Gly Lys Val Thr Ile Gln Ile Asp
                85                  90                  95

Arg Val Val Met Leu Gly Ala Val Ala Gly Glu
            100                 105

<210> SEQ ID NO 11
<211> LENGTH: 107
<212> TYPE: PRT
<213> ORGANISM: Arabidopsis Thaliana

<400> SEQUENCE: 11

Ala Glu Phe Leu Leu Gln Cys Leu Pro Gly Thr Leu Val Val Thr Ile
1               5                   10                  15

Lys Arg Gly Asn Asn Met Lys Gln Ser Val Gly Asn Pro Ser Val Phe
            20                  25                  30

Cys Lys Ile Thr Leu Gly Asn Asn Pro Pro Arg Gln Thr Lys Val Ile
        35                  40                  45

Ser Thr Gly Pro Asn Pro Glu Trp Asp Glu Ser Phe Ser Trp Ser Phe
    50                  55                  60

Glu Ser Pro Pro Lys Gly Gln Lys Leu His Ile Ser Cys Lys Asn Lys
65                  70                  75                  80

Ser Lys Met Gly Lys Ser Ser Phe Gly Lys Val Thr Ile Gln Ile Asp
                85                  90                  95

Arg Val Val Met Leu Gly Ala Val Ala Gly Glu
            100                 105

<210> SEQ ID NO 12
<211> LENGTH: 107
<212> TYPE: PRT
<213> ORGANISM: Ricinus communis

<400> SEQUENCE: 12

Ala Glu Phe Leu Leu Gln Cys Leu Pro Gly Thr Leu Val Val Ile Ile

```
                1               5                   10                  15
            Lys Arg Gly Asn Asn Met Lys Gln Ser Val Gly Asn Pro Ser Val Tyr
                        20                  25                  30

Cys Lys Leu Thr Leu Gly Asn Thr Pro Arg Gln Thr Lys Val Val
                        35                  40                  45

Ser Thr Gly Pro Asn Pro Glu Trp Asp Glu Ser Phe Ala Trp Ser Phe
                    50                  55                  60

Glu Ser Pro Pro Lys Gly Gln Lys Leu His Ile Ser Cys Lys Asn Lys
            65                  70                  75                  80

Ser Lys Met Gly Lys Ser Ser Phe Gly Lys Val Thr Ile Gln Ile Asp
                        85                  90                  95

Arg Val Val Met Leu Gly Ala Val Ala Gly Glu
                        100                 105
```

<210> SEQ ID NO 13
<211> LENGTH: 107
<212> TYPE: PRT
<213> ORGANISM: Populus trichocarpa

<400> SEQUENCE: 13

```
            Ala Glu Phe Leu Leu Gln Cys Leu Pro Gly Thr Leu Val Val Ile Ile
            1               5                   10                  15

Lys Arg Gly Asn Asn Met Lys Gln Ser Val Gly Asn Pro Ser Val Tyr
                        20                  25                  30

Cys Lys Ile Thr Leu Gly Ser Thr Pro Pro Arg Gln Thr Lys Val Val
                        35                  40                  45

Ser Thr Gly Pro Asn Pro Glu Glu Glu Ser Phe Ser Trp Ser Phe
                    50                  55                  60

Glu Ser Pro Pro Lys Gly Gln Lys Leu His Ile Ser Cys Lys Asn Lys
            65                  70                  75                  80

Ser Lys Met Gly Lys Ser Ser Phe Gly Lys Val Thr Ile Gln Ile Asp
                        85                  90                  95

Arg Val Val Met Leu Gly Ala Val Ala Gly Glu
                        100                 105
```

<210> SEQ ID NO 14
<211> LENGTH: 107
<212> TYPE: PRT
<213> ORGANISM: Vitis vinifera

<400> SEQUENCE: 14

```
            Ala Glu Phe Leu Leu Gln Cys Leu Pro Gly Thr Leu Leu Val Thr Ile
            1               5                   10                  15

Lys Arg Gly Asn Asn Met Lys Gln Ser Val Gly Asn Pro Ser Val Phe
                        20                  25                  30

Cys Lys Leu Thr Leu Ala Asn Thr Pro Ala Arg Gln Thr Lys Val Val
                        35                  40                  45

Ser Thr Gly Pro Asn Pro Glu Trp Asp Glu Ser Phe Ala Trp Thr Phe
                    50                  55                  60

Glu Ser Pro Pro Lys Gly Gln Lys Leu Asn Ile Ser Cys Lys Asn Lys
            65                  70                  75                  80

Ser Lys Met Gly Lys Ser Ser Phe Gly Lys Val Thr Ile Gln Ile Asp
                        85                  90                  95

Arg Val Val Met Leu Gly Thr Val Ala Gly Glu
                        100                 105
```

<210> SEQ ID NO 15
<211> LENGTH: 107
<212> TYPE: PRT
<213> ORGANISM: Cicer arietinum

<400> SEQUENCE: 15

Ala Glu Phe Leu Leu Gln Cys Leu Pro Gly Thr Leu Val Val Ile Ile
1               5                   10                  15

Lys Arg Gly Asn Asn Met Lys Gln Ser Val Gly Asn Pro Ser Val Tyr
            20                  25                  30

Cys Lys Ile Thr Leu Gly Asn Asn Pro Pro Arg Leu Thr Lys Val Val
        35                  40                  45

Ser Thr Gly Pro Asn Pro Glu Trp Asp Glu Ser Phe Ser Trp Ser Phe
    50                  55                  60

Glu Ser Pro Pro Lys Gly Gln Lys Leu His Ile Ser Cys Lys Asn Lys
65                  70                  75                  80

Ser Lys Val Gly Lys Ser Lys Phe Gly Lys Val Thr Ile Gln Ile Asp
                85                  90                  95

Arg Val Val Met Leu Gly Ala Val Ala Gly Glu
            100                 105

<210> SEQ ID NO 16
<211> LENGTH: 107
<212> TYPE: PRT
<213> ORGANISM: Oryza sativa

<400> SEQUENCE: 16

Ala Glu Leu Leu Leu Gln Cys Leu Pro Gly Thr Leu Thr Val Thr Ile
1               5                   10                  15

Lys Arg Gly Asn Asn Leu Arg Gln Ser Val Gly Asn Pro Ser Ala Phe
            20                  25                  30

Cys Lys Leu Thr Leu Gly Asn Asn Pro Pro Arg Leu Thr Lys Thr Val
        35                  40                  45

Ser Thr Cys Ala Thr Pro Glu Trp Asp Glu Ala Phe Ala Trp Ala Phe
    50                  55                  60

Asp Ser Pro Pro Lys Gly Gln Lys Leu His Ile Ser Cys Lys Asn Lys
65                  70                  75                  80

Ser Lys Val Gly Lys Ser Lys Phe Gly Lys Val Thr Ile Gln Ile Asp
                85                  90                  95

Arg Val Val Met Leu Gly Ala Val Ala Gly Glu
            100                 105

<210> SEQ ID NO 17
<211> LENGTH: 107
<212> TYPE: PRT
<213> ORGANISM: Zea mays

<400> SEQUENCE: 17

Ala Asp Ser Leu Leu His Cys Leu Pro Cys Cys Leu Thr Val Thr Ile
1               5                   10                  15

Ile Arg Gly Asn Asn Leu Lys Gln Thr Met Gly Gly Thr Asn Ala Phe
            20                  25                  30

Cys Cys Leu Gln Ile Gly Asn Gly Pro Pro Arg Gln Thr Lys Val Val
        35                  40                  45

Asn His Ser Met Cys Pro Ala Trp Asn Glu Gly Phe Thr Trp Leu Phe
    50                  55                  60

Asp Val Ala Pro Lys Gly Gln Lys Leu Tyr Ile Ile Cys Lys Ser Lys
65                  70                  75                  80

```
Asn Thr Phe Gly Lys Ser Thr Leu Gly Arg Val Thr Ile Gln Ile Asp
                85                  90                  95

Lys Val Val Thr Glu Gly Val Tyr Ser Gly Phe
            100             105
```